United States Patent [19]

Mikkelsen

[11] Patent Number: Plant 5,538

[45] Date of Patent: Aug. 20, 1985

[54] BEGONIA PLANT NAMED TANGO

[75] Inventor: James C. Mikkelsen, Ashtabula, Ohio

[73] Assignee: Mikkelsens, Inc., Ashtabula, Ohio

[21] Appl. No.: 547,722

[22] Filed: Nov. 1, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of begonia plant named Tango characterized by its relatively large, full semiball shaped double flowers with ruffled edges, uniform deep peach-pink flower color, slow and compact growth habit, firm foliage, excellent propagation by leaf or stem cuttings, and by its excellent keeping qualities.

1 Drawing Figure

The present invention relates to a new and distinctive cultivar of begonia plant, botanically known as *Hiemalis begonia, Fotsch,* and known by the cultivar name Tango.

The new cultivar Tango derived from a lineage of mutations from the cultivar Baluga, disclosed in U.S. Plant Pat. No. 4,127. Tango was observed in a group of 10 cm. flowering plants during the winter of 1981/82, and was identified as number 82-2331. Asexual reproduction by stem and/or leaf cuttings has reproduced the unique features of the new cultivar through successive propagations.

The following characteristics distinguish Tango from both its parents and other begonias commercially known and used in the floriculture industry:

1. The most outstanding characteristic of Tango is the full semiball shaped double flowers with ruffled edges on the tepals. It has little tendency to show open centers as does Baluga.

2. The flower color tends to be quite uniform during flowering period whereas Baluga tends to be in transition from start to end of flowering.

3. The flower color is a deep peach or apricot pink that blends well with yellow to red color schemes in decorations.

4. Like Baluga, growth is slow and compact, making Tango ideal for small pot (10 cm.) plant production.

5. Foliage is firm and clean, giving the plant a crisp appearance.

6. Propagation is excellent by either leaf or stem cuttings. The plant illustrated was grown from a leaf cutting and demonstrates good adventitious bud development from base of leaf petiole.

7. Flower size is larger than Baluga, but the new cultivar appears to be less floriferous than Baluga. However, flower size and form gives a more distinct showing of the inflorescence.

8. The keeping qualities of the flower are excellent, with less sun scalding or botrytis problems than the most double type hiemalis begonias.

The accompanying colored photograph taken in May 1983 illustrates in perspective the overall appearance of Tango, showing the colors as true as it is reasonably possible to obtain in a colored reproduction of this type.

The following is a detailed description of my new begonia cultivar based on plants produced under commercial practices in the greenhouses of Mikkelsens, Inc., Ashtabula, Ohio, and grown in 10 cm. pots using a multi-shooted plant propagated from a leaf cutting. Color references are made to The Royal Horticultural Society Colour Chart except where general color terms of ordinary dictionary significance are used. Light, temperature, and nutrition may alter visual coloration of foliage and flowers.

Parentage:

A selection from a lineage of spontaneous mutations from the cultivar Baluga, and identified as number 82-2331.

Propagation:

(A) *Type cutting.*—Leaf cutting.

(B) *Time to root.*—21 days at 22° C. summer; 24–28 days at 20°–22° C. winter.

(C) *Rooting habit.*—Fibrous, dendritic.

(D) *Time for shoot development.*—From sticking leaf cutting to shoots 5 cm. high, 65 days in summer. Consistantly 5–7 shoots.

Plant description:

(A) *Form.*—Basically upright, self branching, compact.

(B) *Habit of growth.*—Free growing, but close internoded; short, compact, and mounded.

(C) *Foliage.*—Leaves are closely internoded, alternate, tend to be coriaceous. (1) Size: Average 6–7 cm. across×7–8 cm. long; frequently larger, up to 10 cm. in each direction. (2) Shape: Ovate to orbicular. (3) Texture: Firm, crisp, top side glabrous, underside rugose. (4) Margin: Serrated to crenate. (5) Color: Young foliage, top side green 137A, under side yellow green 147B & C; mature foliage, top side yellow green 147A to 137B, under side yellow green 147B-C with slight red infusion. (6) Venation: Palmate.

Flowering description:

(A) *Flowering habits.*—Inflorescence tends to be clustered close to foliage; coloration is uniform in any season but variable to total light and temperature on seasonal basis.

(B) *Natural flowering season.*—Indeterminate; flowering occurs in all seasons; uniformity and amount of flowering affected by day length and temperatures.

(C) *Flower bud description.*—Buds flat, ovate from 20–25 mm. in diameter before opening.

(D) *Flowers borne.*—On strong upright peduncles, appearing semiball shaped with ruffled camellia type flowers; carried close to foliage and maintaining strong coloration.

(E) *Quantity.*—Not as floriferous as Ballet (U.S. Plant Pat. No. 4,743), the yellow mutation of Baluga, and less floriferous than Baluga itself.

(F) *Tepals.*—Outer tepal in tight bud, topside red 40B, underside 42A. (1) Shape: Ovate with ruffled edges. (2) Color, top side in winter when opening: red 41B, fading to red 41C; in summer fading to red 41D, under side red 38B. (3) Number of tepals: As shown, up to 30 or more. (4) Size of tepals: As shown, outer to 35 mm., inner to 20 mm. (5) Flower size: As shown, to 5 cm. when fully open.

(G) *Reproductive organs.*—Sterile triploid.

Disease resistance:

By observations to date, more resistant to mildew than most hiemalis begonias.

I claim:

1. A new and distinct cultivar of begonia plant named Tango, as described and illustrated, and particularly characterized by its relatively large, full semiball shaped double flowers with ruffled edges; uniform deep peach-pink flower color; slow and compact growth habit; firm foliage; excellent propagation by leaf or stem cuttings, and by its excellent keeping qualities.

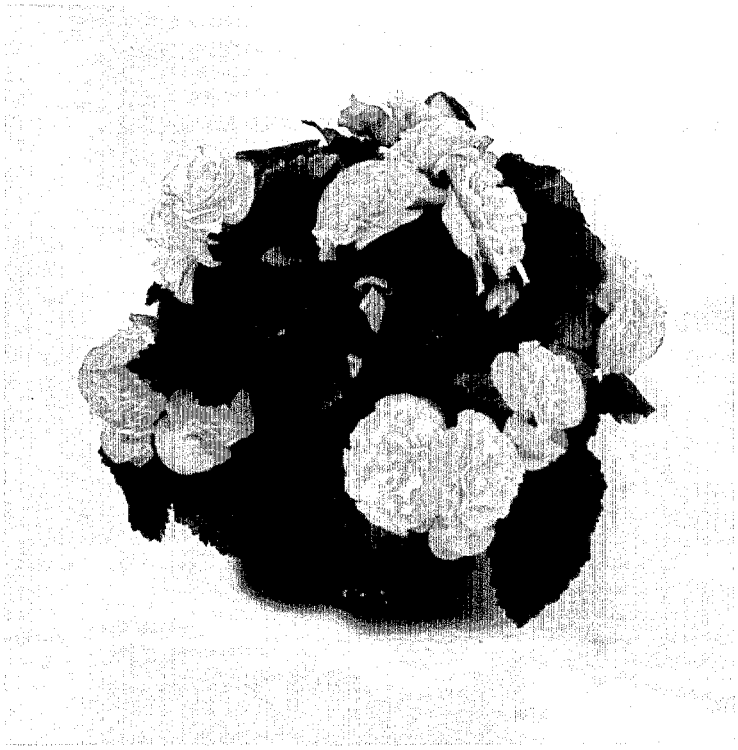

* * * * *